(12) United States Patent
Russell et al.

(10) Patent No.: US 7,326,188 B1
(45) Date of Patent: Feb. 5, 2008

(54) ANESTHESIA MANIFOLD AND INDUCTION VALVE

(75) Inventors: Michael A. Russell, Cohasset, MA (US); Claude A. Vidal, Santa Barbara, CA (US); Russell J. Redmond, Santa Barbara, CA (US); David A. Chandos, North Richland Hills, TX (US); Menachem Zucker, K. Motzkin (IL)

(73) Assignee: Elcam Medical (IL)

( * ) Notice: Subject to any disclaimer, the term of this patent is extended or adjusted under 35 U.S.C. 154(b) by 78 days.

(21) Appl. No.: 10/634,513

(22) Filed: Aug. 4, 2003

Related U.S. Application Data

(60) Provisional application No. 60/417,422, filed on Oct. 9, 2002, provisional application No. 60/401,019, filed on Aug. 2, 2002.

(51) Int. Cl.
*A61M 5/00* (2006.01)
(52) U.S. Cl. .................................... 604/248
(58) Field of Classification Search ............ 604/6.1, 604/9, 30, 31, 32, 33, 34, 99.02, 99.03, 99.04, 604/167.03, 167.04, 167.05, 236, 237, 247, 604/248, 249, 288.03, 320, 323, 335, 246
See application file for complete search history.

(56) References Cited

U.S. PATENT DOCUMENTS

| | | | |
|---|---|---|---|
| 3,782,282 A | 1/1974 | Naftulin et al. | |
| 3,889,710 A | 6/1975 | Brost | |
| 3,954,121 A | 5/1976 | Kardos | |
| 4,031,891 A | 6/1977 | Jess | |
| 4,063,555 A | 12/1977 | Ulinder | |
| 4,141,379 A | 2/1979 | Manske | |
| 4,222,407 A | 9/1980 | Ruschke et al. | |
| 4,333,457 A | 6/1982 | Margulies | |
| 4,369,812 A | 1/1983 | Paradis et al. | |
| 4,447,230 A | 5/1984 | Gula et al. | |
| 4,483,287 A * | 11/1984 | Monigold et al. | .... 123/198 DB |
| 4,512,764 A | 4/1985 | Wunsch | |
| 4,526,140 A * | 7/1985 | Monigold et al. | ....... 123/41.15 |
| 4,556,086 A | 12/1985 | Raines | |
| 4,559,036 A | 12/1985 | Wunsch | |
| 4,768,518 A * | 9/1988 | Peltonen | ..................... 600/490 |

(Continued)

*Primary Examiner*—Manuel Mendez
(74) *Attorney, Agent, or Firm*—Hoffman, Wasson & Gitler, P.C.

(57) ABSTRACT

The present invention is directed to an improved anesthesia manifold and an improved induction valve mechanism. A plurality of induction valve elements may be joined or "ganged" together in order to define a manifold. In the preferred embodiment of the induction manifold, at least two individual valve elements are combined to form the manifold. Each of the plurality of valve elements includes the following components: (1) a valve body; (2) a first inlet port carried by the valve body and defining at least in part a central fluid communication flow path for supplying intravenous fluid to patient; and (3) a second inlet port carried said valve body and at least in part defining an anesthesia drug inlet. Each of the plurality of valve components: (1) an induction valve mechanism which maintains said second inlet port in a closed condition until a predetermined amount of pressure is applied thereto; (2) a back flow valve mechanism which maintains said induction valve components in open condition to permit at least one of the following operations: (a) aspiration; (b) back flow; (c) purging; and (d) sampling.

Additionally, a control mechanism is provided for each of the plurality of individual valve components to actuate said induction valve mechanism and said backflow valve mechanism.

6 Claims, 3 Drawing Sheets

U.S. PATENT DOCUMENTS

| | | |
|---|---|---|
| 4,795,441 A | 1/1989 | Bhatt |
| 4,915,688 A | 4/1990 | Bischof et al. |
| 4,922,954 A | 5/1990 | Blomquist et al. |
| 4,946,448 A | 8/1990 | Richmond |
| 4,988,062 A | 1/1991 | London |
| 5,020,562 A | 6/1991 | Richmond et al. |
| 5,074,334 A * | 12/1991 | Onodera ................ 137/625.41 |
| 5,092,842 A | 3/1992 | Bechtold et al. |
| 5,105,853 A | 4/1992 | Lie |
| 5,188,591 A | 2/1993 | Dorsey, III |
| 5,190,525 A | 3/1993 | Oswald et al. |
| 5,205,834 A | 4/1993 | Moorehead et al. |
| 5,288,290 A * | 2/1994 | Brody ........................ 604/32 |
| 5,308,322 A | 5/1994 | Tennican et al. |
| 5,353,837 A | 10/1994 | Faust |
| 5,356,375 A | 10/1994 | Higley |
| 5,429,485 A | 7/1995 | Dodge |
| 5,431,185 A | 7/1995 | Shannon et al. |
| 5,439,451 A | 8/1995 | Collinson et al. |
| 5,535,771 A | 7/1996 | Purdy et al. |
| 5,618,268 A | 4/1997 | Raines et al. |
| 5,676,346 A | 10/1997 | Leinsing |
| 5,697,904 A | 12/1997 | Raines et al. |
| 5,738,662 A | 4/1998 | Shannon et al. |
| 5,788,215 A | 8/1998 | Ryan |
| 5,806,551 A | 9/1998 | Meloul et al. |
| 5,817,068 A * | 10/1998 | Urrutia ........................ 604/248 |
| 5,873,731 A | 2/1999 | Prendergast |
| 5,935,112 A | 8/1999 | Stevens et al. |
| 6,009,902 A | 1/2000 | Troiani et al. |
| 6,099,511 A * | 8/2000 | Devos et al. ................ 604/246 |
| 6,117,114 A | 9/2000 | Paradis |
| 6,171,287 B1 | 1/2001 | Lynn et al. |
| 6,245,048 B1 | 6/2001 | Fangrow et al. |
| 6,364,861 B1 | 4/2002 | Feith et al. |
| 6,482,188 B1 | 11/2002 | Rogers et al. |
| 6,575,187 B2 * | 6/2003 | Leys et al. ................ 137/15.21 |
| 6,638,258 B2 * | 10/2003 | Schwartz et al. ........... 604/247 |
| 6,971,999 B2 | 12/2005 | Py et al. |
| 6,991,215 B2 | 1/2006 | Kiehne |
| 2002/0147431 A1 | 10/2002 | Lopez et al. |

* cited by examiner

ANESTHESIA MANIFOLD AND INDUCTION VALVE

REFERENCE TO RELATED APPLICATIONS

This application claims the benefit of U.S. Provisional Patent Application Ser. No. 60/417,422, filed 9 Oct. 2002, entitled "Anesthesia Manifold"; and U.S. Provisional Patent Application Ser. No. 60/401,019, filed 2 Aug. 2002, entitled "Anesthesia Manifold." These provisional applications are incorporated herein as if fully set forth.

FIELD OF THE INVENTION

This invention pertains to a novel valve and valve manifold to facilitate liquid anesthesia induction.

BACKGROUND OF THE INVENTION

Increasingly, anesthesiologists use liquid anesthetic agents, administered intravenously. This technique allows for faster anesthesia induction and faster corrective action if a patient shows sign of adverse reaction to the anesthesia. At the onset of the procedure, an intravenous (IV) catheter is inserted in a vein and connected to an IV bag providing a constant drip of saline via an IV line including one or, typically more, access sites for drug administration via syringes and/or IV pumps.

Many such systems incorporate stopcocks, most frequently ganged together into a manifold configuration. While such devices function well, they require many handle manipulations. Such manipulations are not only tedious but they also can lead to errors. For instance, manipulating the handles of a stopcock manifold in the wrong way can result in the inadvertent dilution of a drug contained in a syringe attached to one of the ports.

Because of their need for a more-user-friendly valve system, anesthesiologists have elected to use pressure or luer-activated valves because such valves are easier to use (one handed procedure and less risk of error). However pressure activated valves do not allow for gravity infusions or for aspiration. Luer activated valves alone do not prevent retrograde flow when activated.

Thus, there is a growing need for better valves and valve manifolds for use in anesthesia. This disclosure describes a new concept aimed at facilitating anesthesia induction without the drawbacks of the existing valve systems.

SUMMARY OF THE INVENTION

The present invention is directed to an improved anesthesia manifold and an improved induction valve mechanism. A plurality of induction valve elements may be joined or "ganged" together in order to define a manifold. In the preferred embodiment of the induction manifold, at least two individual valve elements are combined to form the manifold. Each of the plurality of valve elements includes the following components: (1) a valve body; (2) a first inlet port carried by the valve body and defining at least in part a central fluid communication flow path for supplying intravenous fluid to patient; and (3) a second inlet port carried by the valve body and at least in part defining an anesthesia drug inlet. Each of the plurality of valve components include: (1) an induction valve mechanism which maintains the second inlet port in a closed condition until a predetermined amount of pressure is applied thereto; and (2) a back flow valve mechanism which maintains the induction valve components in open condition to permit at least one of the following operations: (a) aspiration; (b) back flow; (c) purging; and (d) sampling.

Additionally, a control mechanism is provided for each of the plurality of individual valve components to actuate the induction valve mechanism and the backflow valve mechanism.

BRIEF DESCRIPTION OF THE DRAWINGS

The present invention will be understood and appreciated more fully from the following detailed description, taken in conjunction with the drawings in which.

DETAILED DESCRIPTION OF THE INVENTION

The present invention is directed to an improved valve manifold for use in delivering liquid anesthesia. The invention includes novel valve elements which can be "ganged" together to constitute a manifold. The embodiment described in this application has several operational attributes, including: (1) the manifold is made up of a plurality of independently-operable valve elements; (2) each valve can be individually controlled and moved between any one of a plurality of predefined operating modes; and (3) the two basic modes of operation include a pressure-activated flow mode of operation, and an aspiration/backflow/purge/sample mode of operation.

In operation, anesthesia drugs are administered through each individual valve of the valve manifold. The valve allows the anesthesia drug to mix into an IV line which receives a saline drip from an IV bag and delivers the mixture of saline fluid and the anesthesia drug to the patient intravenously through an IV catheter.

In the pressure-activated flow mode of operation, an individual valve is connected to a syringe which is utilized to push anesthesia drug through the individual valve into the IV line. Alternatively, it may be coupled to an IV pump. In this mode of operation, the valve is in a closed condition until a sufficient amount of pressure is applied to a pressure-responsive valve member. In this particular application, the actuation of the syringe or the operation of the IV pump generates pressure sufficient to actuate the valve and allow the anesthesia drug to pass through the valve into the IV line. The valve element also operates to check or prevent retrograde flow through the valve.

In the aspiration/backflow/purge/sample mode of operation, an individual valve is utilized to withdraw fluids from the patient through the IV line, to allow aspiration of the valve and IV line, to purge the valve, or to obtain a blood sample. The aspiration/backflow/purge/sample mode of operation can be utilized to withdraw samples, typically utilizing a syringe.

In a preferred embodiment of the present invention, the individual valve members require that some component be moved in order to switch the valve between the modes of operation.

Figure 1:
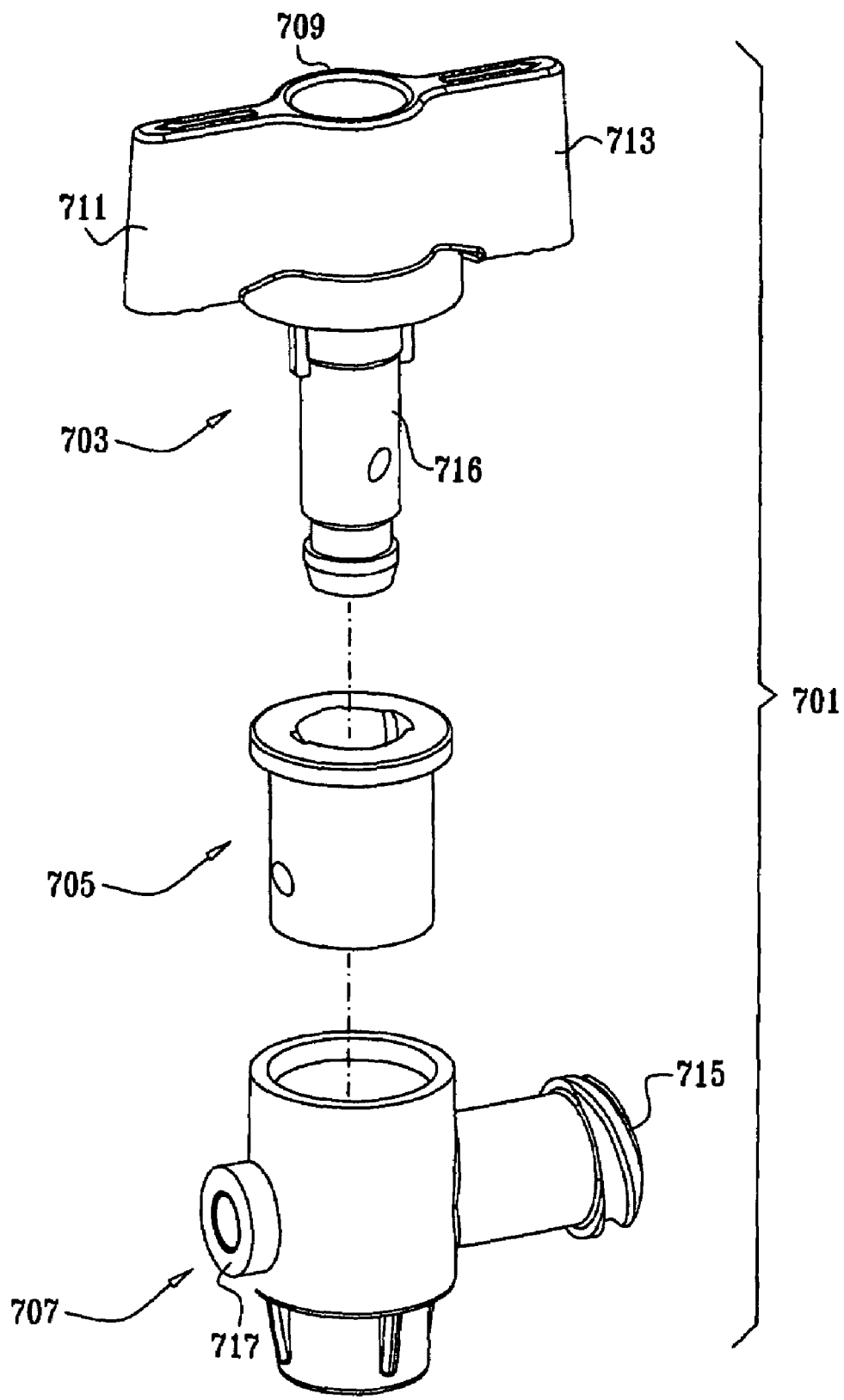
FIG. 1 depicts the components which make up a preferred embodiment of the present invention in exploded view form.
Figure 2:
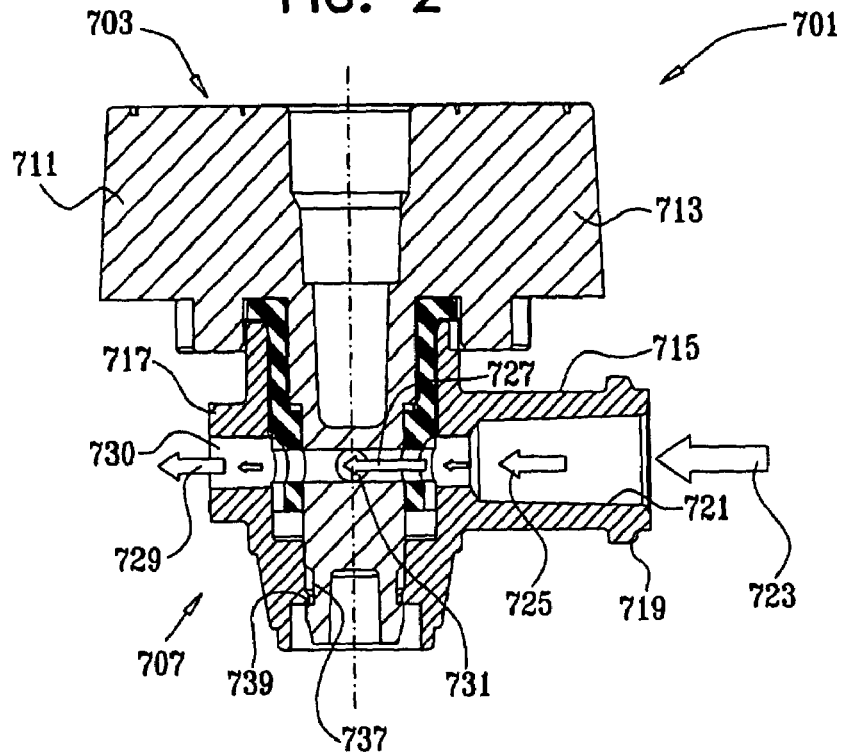
FIG. 2 is a partial longitudinal section view of a portion of the preferred embodiment.
Figure 3:
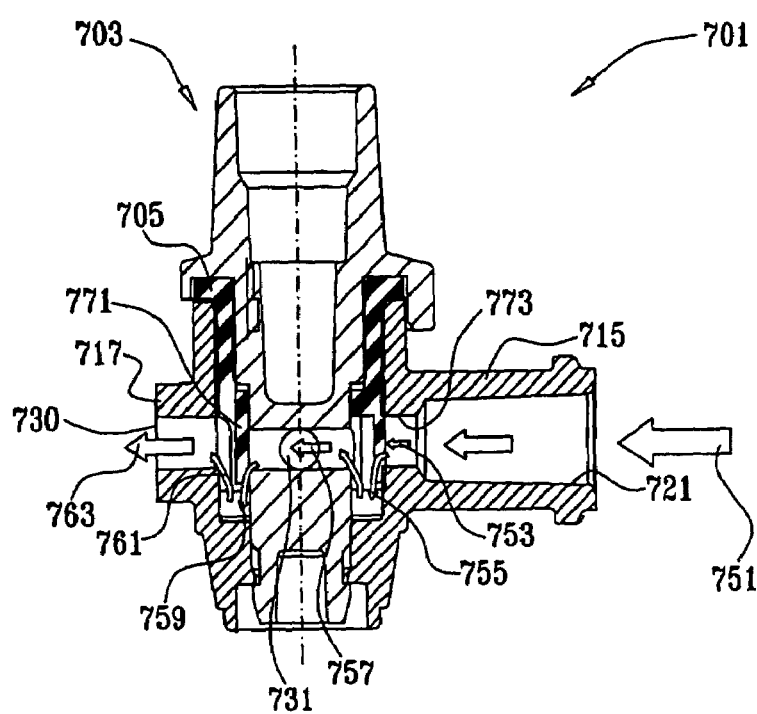
FIG. 3 is a partial longitudinal section view of a portion of the preferred embodiment.
Figure 4:
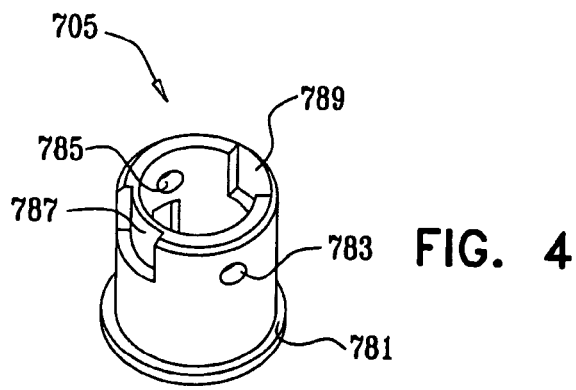
FIG. 4 is a perspective view of the ring component shown in FIG. 1.
Figure 5:
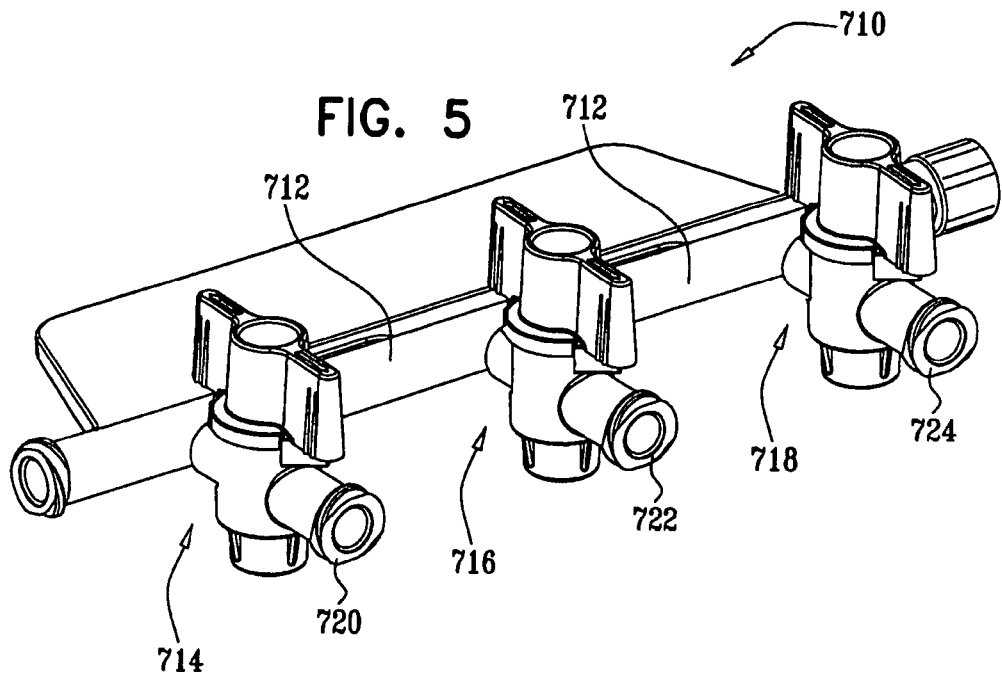
FIG. 5 is a pictorial representation of a manifold formed with a number of the valves "ganged" together.

A preferred embodiment of the present invention is depicted in FIGS. 1-6. FIG. 1 depicts the components which make up the preferred embodiment in exploded view form. FIG. 2 is a partial longitudinal section view of a portion of the preferred embodiment. In the view of FIG. 2, the valve is depicted in an aspiration/backflow/purge/sample mode of operation. In contrast, FIG. 3 is a partial longitudinal section view of a portion of the preferred embodiment; however, FIG. 3 depicts the apparatus in a pressure-activated flow mode of operation. FIG. 4 is a perspective view of a ring component of FIG. 1. FIG. 5 is a pictorial representation of a manifold formed with a number of the valves "ganged" together.

With reference now to FIG. 1, the preferred embodiment will now be described. A valve 701 is made up of three major components: a core 703, a ring 705, and a body 707. The core 703 includes a manually-operable portion 709 with outwardly extending "wings" 711 and 713 which are adapted to be gripped by thumb and forefinger of an operator. The core may be rotated between two positions, each position corresponding to an operating mode. When the "wings" 711 and 713 are aligned as shown in FIG. 2, the valve is in an aspiration/backflow/purge/sample mode of operation. When the "wings" 711 and 713 are positioned orthogonal to the position of FIG. 2, the valve is in a pressure-activated flow mode of operation. The core 703 further includes a contoured lower portion 716 which is adapted to extend through the central bore of ring 705 and to secure the ring from rotating relatively to the core, with components maintained within the cavity of body 707. Body 707 includes an inlet 715 which is adapted for the receipt of anesthesia drugs or other fluids which are to be administered to a patient, and an outlet 717 which allows flow through the manifold and toward the patient. In the aspiration/backflow/purge/sample mode of operation, fluids may be pulled from the manifold in reverse direction, flowing from outlet 717 toward inlet 715.

With reference now to FIG. 2, the aspiration/backflow/purge/sample mode of operation will now be described. In this view, inlet 715 is shown as including an external female connector 719 and a central cavity 721. Outlet 717 includes a central cavity 730. As shown in this view, flow arrows 723, 725, 727, and 729 depict a possible flow inward through valve 701. In this configuration, fluid may also flow in the reverse direction from outlet 717 to inlet 715. Core 703 is shown as including a central cavity 731 which aligns with inlet 715 and outlet 717 when the "wings" 711 and 713 of core 703 are aligned with inlet and outlet ports 715 and 717. In this configuration, the ring 705 of FIG. 1 does not interfere with the inward or outward flow of fluid through valve 701. FIG. 2 also depicts the manner by which core 703 is secured in position relative to body 707. More specifically, a circular notch 737 is provided on the exterior surface of core 703 at its distal end. A corresponding shoulder 739 is formed in the central cavity of body 707 and adapted in size and location in order to mate with circular notch 737.

FIG. 3 depicts valve 701 in a pressure-activated flow mode of operation. In this configuration, ring 705 operates to permit the flow of fluid in one direction only and to check the flow of fluid in the opposite direction. As seen in FIG. 3, flow arrows 751, 753, 755, 757, 759, 761, and 763 depict the flow of fluid through valve 701 in this particular mode of operation. As shown, ring 705 includes flaps, 771 and 773, which extend downward into the flowpath when the core 703 is rotated to change the mode of operation. Flaps 771 and 773 are adapted to move easily in response to one flow direction, but to oppose flow in the opposite direction. For example, flap 773 is adapted to be in close physical proximity to flow channel 721 of inlet 715. Fluid flowing inward through inlet 715 will push flap 773 radially inward and will flow under and around flap 773. In the event of backflow, flap 773 will be pushed into sealing engagement with cavity 721, thus checking backflow. Likewise, flap 771 is in close physical proximity to cavity 731 of core 703. Flap 771 will move radially outward in response to flow moving from inlet 715 to outlet 717. Fluid will urge flap 771 radially outward and will flow around flap 771. However, flap 771 will check the reverse flow by sealing engagement of flap 771 to cavity 731 of core 703. Note that there is an asymmetry between flaps 773 and 771. This asymmetry facilitates the operation of the valve during the pressure activated flow mode. In alternative embodiment, it may be possible to utilize only a single flap. In such an alternative, flap 771 is likely excluded and flap 773 is utilized solely to preferentially direct the flow of fluid inward in response to the pressure from fluid at inlet 715 and to check the flow of fluid backward through valve 701.

FIG. 4 depicts ring 705 in a perspective view. As is shown, a shoulder 781 is provided at the upper end of ring 705 to engage body 707. Cavities 783 and 785 are provided to allow fluid to pass through ring 705 during the aspiration/backflow/purge/sample mode of operation. Cavities 787 and 789 are provided at the lower portion of ring 705 in order to define flaps 771 and 773.

FIG. 5 is a pictorial representation of an anesthesia manifold formed through the "ganging" together of valves 714, 716 and 718. A manifold 710, including a central flow member 712, is mechanically coupled to the outlet ports of valves 714, 716 and 718. Inlet ports 720, 722 and 724 are adapted to mate with syringes or medication pumps in order to supply medication and/or fluids to the manifold 710. In this view, the wings 711 and 713 of the valves 714, 716 and 718 are shown as being aligned with the inlet ports 720, 722 and 724, respectively, so that valves 714, 716 and 718 are in the aspiration/backflow/purge/sample mode of operation.

Figure 6:
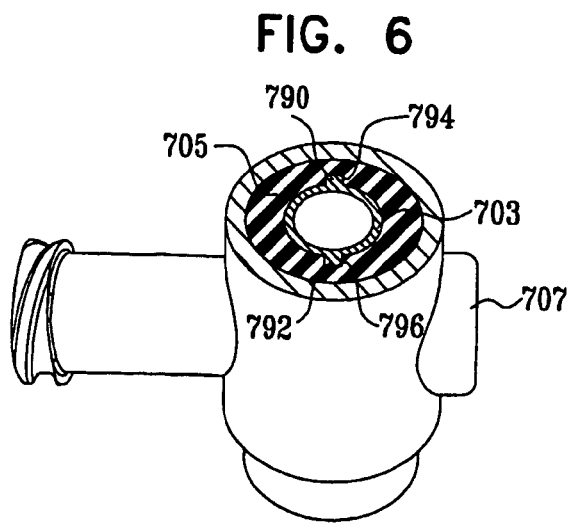
FIG. 6 is a pictorial representation of an anti-rotational interlock feature.

FIG. 6 is a pictorial representation of an anti-rotational interlock feature 801 of the present invention. As seen in FIG. 6, the core 703 is disposed within a central cavity defined within ring 705. Ring 705 is disposed within a central cavity of body 707. Ribs 790 and 792 are formed on the exterior surface of core 703. They extend along at least a substantial portion of the outer surface of core 703. Corresponding slots 794 and 796 are defined within the central bore of ring 705. Ribs 790 and 792 are adapted in size and shape in order to fit within slots 794 and 796. In alternative embodiments, as few as one rib and slot may be utilized to lock the core 703 to ring 705 forcing them to move together as the core is rotated relative to body 707. In yet alternative embodiments, a plurality of ribs and slots may be provided between core 703 and ring 705. In an alternative configuration, the ribs may be provided on ring 705 and the slots may be provided on core 703. This anti-rotational interlock feature 801 ensures that the core 703 and ring 705 are always properly aligned.

Although the invention been described with reference to a particular embodiment, this description is not meant to be construed in a limiting sense. Various modifications of the disclosed embodiments as well as alternative embodiments of the invention will become apparent to persons skilled in the art upon reference to the description of the invention. It is therefore contemplated that the appended claims will cover any such modifications or embodiments that fall within the scope of the invention.

What is claimed is:

1. An anesthesia manifold, comprising a plurality of valves which are mounted onto a manifold element, each of said plurality of valves having a stopcock-type configuration including an inlet adapted to receive fluid to be administered to a patient and an outlet communicating with said manifold element, an open aspiration/backflow/purge/sample operative orientation and a second operative orientation which is pressure responsive for flow from said inlet through said outlet into said manifold element.

2. An anesthesia manifold according to claim 1, and wherein at least one of said plurality of valves comprises an induction valve.

3. An anesthesia manifold according to claim 1, and wherein said manifold element comprises a planar element.

4. An anesthesia manifold according to claim 1, and wherein at least one of said plurality of valves also includes a seal element, said seal element including a flap portion which is adapted to flex under pressure, thereby opening said valve.

5. An anesthesia manifold according to claim 4, and wherein at least one of said plurality of valves comprises a central element including a handle portion, said handle portion having a first handle operative orientation enabling said open operative orientation and a second handle operative orientation enabling said second operative orientation.

6. An anesthesia manifold according to claim 5, and wherein said seal element and said central element are adapted to rotate together, thereby transferring said valve between said open operative orientation and said second operative orientation.

* * * * *